United States Patent
Klein et al.

(10) Patent No.: US 11,684,478 B2
(45) Date of Patent: Jun. 27, 2023

(54) HIGH FATIGUE STRENGTH POROUS STRUCTURE

(71) Applicant: Howmedica Osteonics Corp., Mahwah, NJ (US)

(72) Inventors: Robert W. Klein, Orangeburg, NY (US); Lewis Mullen, Englewood, NJ (US); Joseph Robinson, Ridgewood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 17/716,537

(22) Filed: Apr. 8, 2022

(65) Prior Publication Data

US 2022/0226897 A1   Jul. 21, 2022

Related U.S. Application Data

(62) Division of application No. 15/982,704, filed on May 17, 2018, now Pat. No. 11,298,747.
(Continued)

(51) Int. Cl.
*B33Y 80/00* (2015.01)
*A61F 2/30* (2006.01)
(Continued)

(52) U.S. Cl.
CPC .............. *A61F 2/3094* (2013.01); *B22F 5/10* (2013.01); *B22F 7/004* (2013.01); *B22F 10/28* (2021.01);
(Continued)

(58) Field of Classification Search
CPC .. B22F 10/20; B22F 5/10; B22F 7/004; B22F 2003/247; B22F 10/38; B22F 10/80;
(Continued)

(56) References Cited

U.S. PATENT DOCUMENTS

| | | |
|---|---|---|
| 3,605,123 A | 9/1971 | Pratt et al. |
| 4,164,794 A | 8/1979 | Spector et al. |

(Continued)

FOREIGN PATENT DOCUMENTS

| | | |
|---|---|---|
| CA | 2295896 A1 | 7/2000 |
| CA | 2448592 A1 | 5/2004 |

(Continued)

OTHER PUBLICATIONS

Created and Designed by Shaman Gaspar, Maintained by Peter Fox, "Direct Laser Remelting" , "Project Web Site", Using Lasers to Grow 3D object on Stainless Steel; The University of Liverpool 2002; http://mserc.liv.ac.uk/research/dlr/dlr_html.

(Continued)

*Primary Examiner* — Rebecca Janssen
(74) *Attorney, Agent, or Firm* — Lerner David LLP

(57) ABSTRACT

A porous apparatus includes a first layer and a second layer. The second layer has a plurality of struts. At least some of the struts define a porous geometry defining a plurality of faces, at least one of the plurality of the faces at least partially confronting the first layer. Each face is bounded by intersecting struts at vertices. Less than all of the vertices of each face of the porous geometry at least partially confronting the first layer are connected by a strut to the first layer. A process of producing the at least partially porous structure includes depositing and scanning metal powder layers. At least some of the scanned metal powder layers form either one or both of a portion of a first section of the structure and a portion of a second section of the structure formed by at least the struts defining the porous geometry.

14 Claims, 7 Drawing Sheets

Related U.S. Application Data

(60) Provisional application No. 62/508,058, filed on May 18, 2017.

(51) Int. Cl.
| | | |
|---|---|---|
| *B33Y 10/00* | (2015.01) | |
| *B33Y 70/00* | (2020.01) | |
| *B22F 5/10* | (2006.01) | |
| *B22F 7/00* | (2006.01) | |
| *B22F 10/28* | (2021.01) | |
| *B22F 10/38* | (2021.01) | |
| B23K 15/00 | (2006.01) | |
| B23K 26/342 | (2014.01) | |
| B22F 3/24 | (2006.01) | |
| B22F 10/80 | (2021.01) | |

(52) U.S. Cl.
CPC ............ *B22F 10/38* (2021.01); *B33Y 10/00* (2014.12); *B33Y 70/00* (2014.12); *B33Y 80/00* (2014.12); *A61F 2002/3092* (2013.01); *A61F 2002/30985* (2013.01); *B22F 10/80* (2021.01); *B22F 2003/247* (2013.01); *B23K 15/0086* (2013.01); *B23K 26/342* (2015.10)

(58) Field of Classification Search
CPC ...... B22F 3/1115; B22F 10/28; A61F 2/3094; A61F 2002/3092; A61F 2002/30985; B33Y 10/00; B33Y 70/00; B33Y 80/00; B33Y 50/00; B23K 15/0086; B23K 26/342; Y02P 10/25
See application file for complete search history.

(56) References Cited

U.S. PATENT DOCUMENTS

| | | |
|---|---|---|
| 4,202,055 A | 5/1980 | Reiner et al. |
| 4,247,508 A | 1/1981 | Housholder |
| 4,344,193 A | 8/1982 | Kenny |
| 4,479,271 A | 10/1984 | Bolesky et al. |
| 4,502,161 A | 3/1985 | Wall |
| 4,513,045 A | 4/1985 | Bondoc et al. |
| 4,542,539 A | 9/1985 | Rowe, Jr. et al. |
| 4,636,219 A | 1/1987 | Pratt et al. |
| 4,644,942 A | 2/1987 | Sump |
| 4,659,331 A | 4/1987 | Matthews et al. |
| 4,673,408 A | 6/1987 | Grobbelaar |
| 4,673,409 A | 6/1987 | Van Kampen |
| 4,714,473 A | 12/1987 | Bloebaum |
| 4,714,474 A | 12/1987 | Brooks, Jr. et al. |
| 4,863,538 A | 9/1989 | Deckard |
| 4,944,817 A | 7/1990 | Bourell et al. |
| 4,961,154 A | 10/1990 | Pomerantz et al. |
| 4,969,907 A | 11/1990 | Koch et al. |
| 4,978,355 A | 12/1990 | Frey et al. |
| 4,990,163 A | 2/1991 | Ducheyne et al. |
| 4,997,445 A | 3/1991 | Hodorek |
| 5,002,572 A | 3/1991 | Picha |
| 5,004,476 A | 4/1991 | Cook |
| 5,017,753 A | 5/1991 | Deckard |
| 5,024,670 A | 6/1991 | Smith et al. |
| 5,031,120 A | 7/1991 | Pomerantz et al. |
| 5,034,186 A | 7/1991 | Shimamune et al. |
| 5,053,090 A | 10/1991 | Beaman et al. |
| 5,067,964 A | 11/1991 | Richmond et al. |
| 5,076,869 A | 12/1991 | Bourell et al. |
| 5,080,674 A | 1/1992 | Jacobs et al. |
| 5,108,432 A | 4/1992 | Gustavson |
| 5,147,402 A | 9/1992 | Bohler et al. |
| 5,155,324 A | 10/1992 | Deckard et al. |
| 5,158,574 A | 10/1992 | Stone |
| 5,171,282 A | 12/1992 | Pequignot |
| 5,176,710 A | 1/1993 | Hahn et al. |
| 5,219,362 A | 6/1993 | Tuke et al. |
| 5,282,861 A | 2/1994 | Kaplan |
| 5,287,435 A | 2/1994 | Cohen et al. |
| 5,298,115 A | 3/1994 | Leonard |
| 5,352,405 A | 10/1994 | Beaman et al. |
| 5,358,529 A | 10/1994 | Davidson |
| 5,386,500 A | 1/1995 | Pomerantz et al. |
| 5,398,193 A | 3/1995 | deAngelis |
| 5,443,510 A | 8/1995 | Shetty et al. |
| 5,456,723 A | 10/1995 | Steinemann et al. |
| 5,490,962 A | 2/1996 | Cima et al. |
| 5,496,372 A | 3/1996 | Hamamoto et al. |
| 5,504,300 A | 4/1996 | Devanathan et al. |
| 5,507,815 A | 4/1996 | Wagner et al. |
| 5,518,680 A | 5/1996 | Cima et al. |
| 5,549,700 A | 8/1996 | Graham et al. |
| 5,571,185 A | 11/1996 | Schug |
| 5,616,294 A | 4/1997 | Deckard |
| 5,624,463 A | 4/1997 | Stone et al. |
| 5,640,667 A | 6/1997 | Freitag et al. |
| 5,648,450 A | 7/1997 | Dickens, Jr. et al. |
| 5,665,118 A | 9/1997 | LaSalle et al. |
| 5,702,448 A | 12/1997 | Buechel et al. |
| 5,716,358 A | 2/1998 | Ochoa et al. |
| 5,735,903 A | 4/1998 | Li et al. |
| 5,749,874 A | 5/1998 | Schwartz |
| 5,769,899 A | 6/1998 | Schwartz et al. |
| 5,773,789 A | 6/1998 | Devanathan et al. |
| 5,795,353 A | 8/1998 | Felt |
| 5,824,098 A | 10/1998 | Stein |
| 5,879,387 A | 3/1999 | Jones et al. |
| 5,879,398 A | 3/1999 | Swarts et al. |
| 5,928,285 A | 7/1999 | Bigliani et al. |
| 5,973,222 A | 10/1999 | Devanathan et al. |
| 5,989,472 A | 11/1999 | Ashby et al. |
| 6,042,774 A | 3/2000 | Wilkening et al. |
| 6,046,426 A | 4/2000 | Jeantette et al. |
| 6,049,054 A | 4/2000 | Panchison et al. |
| 6,087,553 A | 7/2000 | Cohen et al. |
| 6,132,468 A | 10/2000 | Mansmann |
| 6,139,585 A | 10/2000 | Li |
| 6,149,689 A | 11/2000 | Grundei |
| 6,206,924 B1 | 3/2001 | Timm |
| 6,215,093 B1 | 4/2001 | Meiners et al. |
| 6,261,322 B1 | 7/2001 | Despres, III et al. |
| 6,261,493 B1 | 7/2001 | Gaylo et al. |
| 6,280,478 B1 | 8/2001 | Richter et al. |
| 6,283,997 B1 | 9/2001 | Garg et al. |
| 6,290,726 B1 | 9/2001 | Pope et al. |
| 6,344,061 B1 | 2/2002 | Leitao et al. |
| 6,355,086 B2 | 3/2002 | Brown et al. |
| 6,371,958 B1 | 4/2002 | Overaker |
| 6,395,327 B1 | 5/2002 | Shetty |
| 6,454,811 B1 | 9/2002 | Sherwood et al. |
| 6,476,343 B2 | 11/2002 | Keicher et al. |
| 6,482,209 B1 | 11/2002 | Engh et al. |
| 6,497,728 B2 | 12/2002 | Yong |
| 6,520,996 B1 | 2/2003 | Manasas et al. |
| 6,530,951 B1 | 3/2003 | Bates et al. |
| 6,551,608 B2 | 4/2003 | Yao |
| 6,558,421 B1 | 5/2003 | Fell et al. |
| 6,592,598 B2 | 7/2003 | Vibe-Hansen et al. |
| 6,626,945 B2 | 9/2003 | Simon et al. |
| 6,632,246 B1 | 10/2003 | Simon et al. |
| 6,652,587 B2 | 11/2003 | Felt et al. |
| 6,676,892 B2 | 1/2004 | Das et al. |
| 6,679,917 B2 | 1/2004 | Ek |
| 6,682,567 B1 | 1/2004 | Schroeder |
| 6,686,437 B2 | 2/2004 | Buchman et al. |
| 6,709,462 B2 | 3/2004 | Hanssen |
| 6,712,822 B2 | 3/2004 | Re et al. |
| 6,716,957 B2 | 4/2004 | Tunc |
| 6,743,232 B2 | 6/2004 | Overaker et al. |
| 6,852,125 B2 | 2/2005 | Simon et al. |
| 6,863,689 B2 | 3/2005 | Ralph et al. |
| 6,866,684 B2 | 3/2005 | Fell et al. |
| 6,911,044 B2 | 6/2005 | Fell et al. |
| 6,932,610 B2 | 8/2005 | Ono et al. |
| 7,051,417 B2 | 5/2006 | Michelson |
| 7,168,283 B2 | 1/2007 | Van Note et al. |

(56) References Cited

U.S. PATENT DOCUMENTS

| | | |
|---|---|---|
| 7,388,972 B2 | 6/2008 | Kitson |
| 7,494,507 B2 | 2/2009 | Dixon et al. |
| 7,497,876 B2 | 3/2009 | Tuke et al. |
| 7,521,017 B2 | 4/2009 | Kunze et al. |
| 7,537,664 B2 | 5/2009 | O'Neill et al. |
| 7,563,284 B2 | 7/2009 | Coppes et al. |
| 7,632,575 B2 | 12/2009 | Justin et al. |
| 7,637,942 B2 | 12/2009 | Mangiardi et al. |
| 7,655,047 B2 | 2/2010 | Swords |
| 7,674,517 B2 | 3/2010 | Ramsey et al. |
| 7,718,109 B2 | 5/2010 | Robb et al. |
| 7,747,305 B2 | 6/2010 | Dean et al. |
| 7,879,275 B2 | 2/2011 | Smith et al. |
| 8,275,594 B2 | 9/2012 | Lin et al. |
| 8,308,807 B2 | 11/2012 | Seebeck et al. |
| 8,350,186 B2 | 1/2013 | Jones et al. |
| 8,430,930 B2 | 4/2013 | Hunt |
| 8,454,705 B2 | 6/2013 | Pressacco et al. |
| 8,551,173 B2 | 10/2013 | Lechmann et al. |
| 8,728,387 B2 | 5/2014 | Jones et al. |
| 8,828,087 B2 | 9/2014 | Stone et al. |
| 8,843,229 B2 | 9/2014 | Vanasse et al. |
| 8,888,862 B2 | 11/2014 | McDonnell et al. |
| 8,903,533 B2 | 12/2014 | Eggers et al. |
| 8,956,364 B2 | 2/2015 | Catanzarite et al. |
| 8,979,936 B2 | 3/2015 | White et al. |
| 8,983,646 B1 | 3/2015 | Hanna |
| 9,011,444 B2 | 4/2015 | Primiano et al. |
| 9,060,788 B2 | 6/2015 | Bollinger |
| 9,066,734 B2 | 6/2015 | Schoenefeld et al. |
| 9,084,618 B2 | 7/2015 | Serbousek et al. |
| 9,113,971 B2 | 8/2015 | Metzger et al. |
| 9,135,374 B2 | 9/2015 | Jones et al. |
| 9,149,282 B2 | 10/2015 | Servidio et al. |
| 9,173,661 B2 | 11/2015 | Metzger et al. |
| 9,173,666 B2 | 11/2015 | Metzger et al. |
| 9,180,010 B2 | 11/2015 | Dong et al. |
| 9,204,977 B2 | 12/2015 | Bollinger |
| 9,237,950 B2 | 1/2016 | Hensley et al. |
| 9,241,745 B2 | 1/2016 | Smith et al. |
| 9,271,744 B2 | 3/2016 | Meridew |
| 9,289,253 B2 | 3/2016 | Vanasse et al. |
| 9,295,497 B2 | 3/2016 | Schoenefeld et al. |
| 9,301,812 B2 | 4/2016 | Kehres et al. |
| 9,339,278 B2 | 5/2016 | Meridew et al. |
| 9,345,548 B2 | 5/2016 | Schoenefeld et al. |
| 9,351,743 B2 | 5/2016 | Kehres et al. |
| 9,386,993 B2 | 5/2016 | Shea et al. |
| 9,364,330 B2 | 6/2016 | Lindsey et al. |
| 9,393,028 B2 | 7/2016 | Schuster |
| 9,408,616 B2 | 8/2016 | Kehres et al. |
| 9,427,320 B2 | 8/2016 | Meridew |
| 9,439,659 B2 | 9/2016 | Schoenefeld et al. |
| 9,445,907 B2 | 9/2016 | Meridew et al. |
| 9,451,973 B2 | 9/2016 | Heilman et al. |
| 9,456,833 B2 | 10/2016 | Maxson et al. |
| 9,456,901 B2 | 10/2016 | Jones et al. |
| 9,814,595 B2 | 11/2017 | Biedermann et al. |
| 10,166,316 B2 | 1/2019 | Landon et al. |
| 2001/0014403 A1 | 8/2001 | Brown et al. |
| 2002/0010512 A1 | 1/2002 | Takei |
| 2002/0015654 A1 | 2/2002 | Das et al. |
| 2002/0016635 A1 | 2/2002 | Despres et al. |
| 2002/0127328 A1 | 9/2002 | Shetty |
| 2002/0130112 A1 | 9/2002 | Manasas et al. |
| 2002/0151983 A1 | 10/2002 | Shetty |
| 2002/0173855 A1 | 11/2002 | Mansmann |
| 2003/0032351 A1 | 2/2003 | Horner et al. |
| 2003/0033018 A1 | 2/2003 | Merchant |
| 2003/0045941 A1 | 3/2003 | Lewallen |
| 2003/0055500 A1 | 3/2003 | Fell et al. |
| 2003/0055501 A1 | 3/2003 | Fell et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0060888 A1 | 3/2003 | Fell et al. |
| 2003/0069638 A1 | 4/2003 | Barlow et al. |
| 2003/0069718 A1 | 4/2003 | Hollister et al. |
| 2003/0153981 A1 | 8/2003 | Wang et al. |
| 2003/0158606 A1 | 8/2003 | Coon et al. |
| 2003/0220696 A1 | 11/2003 | Levine et al. |
| 2004/0000540 A1 | 1/2004 | Soboyejo et al. |
| 2004/0006393 A1 | 1/2004 | Burkinshaw |
| 2004/0009228 A1 | 1/2004 | Tormala et al. |
| 2004/0023586 A1 | 2/2004 | Tilton |
| 2004/0044414 A1 | 3/2004 | Nowakowski |
| 2004/0054416 A1 | 3/2004 | Wyss et al. |
| 2004/0059356 A1 | 3/2004 | Gingras |
| 2004/0098132 A1 | 5/2004 | Andriacchi et al. |
| 2004/0121110 A1 | 6/2004 | Schmidt et al. |
| 2004/0143339 A1 | 7/2004 | Axelson et al. |
| 2004/0153163 A1 | 8/2004 | Posner |
| 2004/0162622 A1 | 8/2004 | Simon et al. |
| 2004/0167633 A1 | 8/2004 | Wen et al. |
| 2004/0191106 A1 | 9/2004 | O'Neill et al. |
| 2004/0199249 A1 | 10/2004 | Fell |
| 2004/0199250 A1 | 10/2004 | Fell |
| 2004/0230315 A1 | 11/2004 | Ek |
| 2004/0243237 A1 | 12/2004 | Unwin et al. |
| 2005/0033424 A1 | 2/2005 | Fell |
| 2005/0043816 A1 | 2/2005 | Datta et al. |
| 2005/0085918 A1 | 4/2005 | Soffiati et al. |
| 2005/0100578 A1 | 5/2005 | Schmid et al. |
| 2005/0123672 A1 | 6/2005 | Justin et al. |
| 2005/0154471 A1 | 7/2005 | Aram et al. |
| 2005/0170159 A1 | 8/2005 | Ramsey et al. |
| 2005/0171604 A1 | 8/2005 | Michalow |
| 2005/0177169 A1 | 8/2005 | Fisher et al. |
| 2005/0192672 A1 | 9/2005 | Wyss et al. |
| 2006/0015187 A1 | 1/2006 | Hunter et al. |
| 2006/0036331 A1 | 2/2006 | Lu et al. |
| 2006/0147332 A1 | 7/2006 | Jones et al. |
| 2006/0241776 A1 | 10/2006 | Brown et al. |
| 2006/0254200 A1 | 11/2006 | Clarke et al. |
| 2007/0142914 A1 | 6/2007 | Jones et al. |
| 2007/0225390 A1 | 9/2007 | Wang et al. |
| 2008/0004709 A1 | 1/2008 | O'Neill et al. |
| 2008/0050412 A1 | 2/2008 | Jones et al. |
| 2008/0161927 A1 | 7/2008 | Savage et al. |
| 2009/0068245 A1 | 3/2009 | Noble et al. |
| 2009/0087605 A1 | 4/2009 | Ramsey et al. |
| 2009/0112315 A1 | 4/2009 | Fang et al. |
| 2010/0298950 A1 | 11/2010 | McDonnell et al. |
| 2011/0014081 A1 | 1/2011 | Jones et al. |
| 2011/0313532 A1 | 12/2011 | Hunt |
| 2012/0067853 A1 | 3/2012 | Wang et al. |
| 2013/0030529 A1 | 1/2013 | Hunt |
| 2013/0056912 A1 | 3/2013 | O'Neill et al. |
| 2013/0123935 A1 | 5/2013 | Hunt et al. |
| 2013/0158672 A1 | 6/2013 | Hunt |
| 2013/0218282 A1 | 8/2013 | Hunt |
| 2013/0264749 A1 | 10/2013 | Jones et al. |
| 2013/0268085 A1 | 10/2013 | Dong et al. |
| 2013/0331949 A1 | 12/2013 | Dehoff et al. |
| 2014/0037873 A1 | 2/2014 | Cheung et al. |
| 2014/0058526 A1 | 2/2014 | Meridew et al. |
| 2014/0121776 A1 | 5/2014 | Hunt |
| 2014/0163445 A1 | 6/2014 | Pallari et al. |
| 2014/0277548 A1 | 9/2014 | Cohen et al. |
| 2014/0288649 A1 | 9/2014 | Hunt |
| 2014/0288650 A1 | 9/2014 | Hunt |
| 2014/0301884 A1 | 10/2014 | Hellestam et al. |
| 2014/0343681 A1 | 11/2014 | Cohen et al. |
| 2015/0018956 A1 | 1/2015 | Steinmann et al. |
| 2015/0134063 A1 | 5/2015 | Steinmann et al. |
| 2016/0098495 A1 | 4/2016 | Dong et al. |
| 2016/0296672 A1 | 10/2016 | Grohowski, Jr. |

(56) References Cited

U.S. PATENT DOCUMENTS

2016/0347464 A1    12/2016  Seack et al.
2018/0021139 A1*    1/2018  Spivack .................. A61L 27/56
                                                            606/331

FOREIGN PATENT DOCUMENTS

| | | |
|---|---|---|
| CN | 101301230 A | 11/2008 |
| CN | 102087676 A | 6/2011 |
| DE | 19502733 A1 | 3/1996 |
| EP | 0 178 650 A2 | 4/1986 |
| EP | 0295038 A2 | 12/1988 |
| EP | 0 528 800 A1 | 3/1993 |
| EP | 0761242 A1 | 3/1997 |
| EP | 1247537 A1 | 10/2002 |
| EP | 1 300 511 A2 | 4/2003 |
| EP | 1418013 A1 | 5/2004 |
| EP | 1426013 A1 | 6/2004 |
| EP | 1455666 A1 | 9/2004 |
| EP | 1493455 A2 | 1/2005 |
| EP | 1683593 A2 | 7/2006 |
| EP | 1800700 A2 | 6/2007 |
| EP | 1806154 A1 | 7/2007 |
| EP | 1949989 A1 | 7/2008 |
| EP | 2022622 A1 | 2/2009 |
| EP | 2606859 A1 | 6/2013 |
| JP | 2255329 A | 10/1990 |
| JP | 4041794 A | 2/1992 |
| JP | 11287020 A | 10/1999 |
| JP | 11348045 A | 12/1999 |
| JP | 2001303751 A | 10/2001 |
| JP | 2003293012 A | 10/2003 |
| JP | 2006158953 A | 6/2006 |
| RU | 2218242 C2 | 12/2003 |
| WO | 9606881 A2 | 3/1996 |
| WO | 02085246 A2 | 10/2002 |
| WO | 2005/084216 A2 | 9/2005 |
| WO | 2005080029 A1 | 9/2005 |
| WO | 2005087982 A1 | 9/2005 |
| WO | 2007058160 A1 | 5/2007 |
| WO | 2009116950 A1 | 9/2009 |
| WO | 2011002765 A2 | 1/2011 |
| WO | 2011060312 A2 | 5/2011 |
| WO | 2013006778 A2 | 1/2013 |

OTHER PUBLICATIONS

Hollander et al., Structural mechanical and in vitro characterization of individually structured Ti-Al-4V produces by direct layer forming, Biomaterials, pp. 1-9, 2005.
Vureal et al., Plasma-sprayed oxide ceramics on steel substrates, Surface Coatings and Technology, 97 (1997) 347-354.
Patello-femoral Arthroplasty X-ray Results, Stryker Howmedica Osteonics, published on or before Apr. 5, 2011.
The Metals Handbook, Desk Edition, 2nd Edition, ASM International, 1998, p. 29.
Meiners et al., "Direct Generation of Metal Parts and Tools by Selective Laser Powder Remelting (SLPR)", W. Meiners, C. Over, K. Wissenbach, R. Poprawe, pp. 655-661 Austin, Texas, Aug. 9-11, 1999.
Hawley's Condensed Chemical Dictionary, 14th edition. John Wiley & Sons, 2002. Definition: sintering.
Dr. Kerron Harvey, producer, Research Intelligence, The University of Liverpool, Issue 13, Jun. 2002.
H.J. Niu and I.T.H. Chang, "Selective Laser Sintering of Gas and Water Atomized High Speed Steel Powders," Scripta Materialia vol. 41, No. 1, (1999), pp. 25-30.
R. Morgan, C.J. Sutcliffe, W. O'Neill, "Experimental investigatoin of nanosecond pulsed Nd:YAG laser re-melted pre-placed powder beds," Rapid Prototyping Journal, vol. 7, No. 3, 2001, pp. 159-172.
N.K. Vail, L.D. Swain, W.C. fox, T.B. Aufdlemorte, G. Lee, J.W. Barlow, "Materials for biomedical applications," Materials and Design, 20, 1999, pp. 123-132.
R.H. Morgan, A.J. Papworth, C. Sutcliffe, P. Fox, W. O'Neill, "High density net shape components by direct laser re-melting of single phase powders," Journal of Materials Science, 37, 2002, pp. 3093-3100.
C.K. Chua et al. Development of a Tissue Engineering Scaffold Structure Library for Rapid Prototyping. Parts 1 and 2, International Journal of Advanced Manufacturing Technology, Feb. 2003, vol. 21, pp. 291-312.
Bobyn et al., "The optimum pore size for the fixation of porous-surfaced metal implants by the ingrowth of bone", Clinical Orthopaedics and Related Research, 150; 263-270 (1980).
Filiz et al., Int. Journal of Machine Tools & Manufacture, 48, 459-472, 2008.
Protek Cementless Replacement of the Acetabulum by E. Morscher, published on or before Apr. 5, 2011.
Chen, "3D Texture Mapping for Rapid Manufacturing", Computer-Aided Design and Applications, University of Southern California, vol. 4, No. 6, pp. 761-771, Jan. 1, 2007.
Engelbrecht et al., Cellular Structures for Optimal Performance, Georgia Institute of Technology & Paramount Industries, Inc., 2009.
Wang, Computer-Aided Design Methods for Additive Fabrication of Truss Structures, Georgia Institute of Technology, 2002.
Extended European Search Report for Application No. EP18173165 dated Sep. 18, 2018.
Tanzer et al, The Hip Society Supplement to the Bone & Joint Journal ; Characterization of bone ingrowth and interface mechanics of a new porous 3D printed biomaterial; vol. 101-B, No. 6, Jun. 2019 ; pp. 62-67.
Stryker Orthopaedics R&D Technical Report; "Porous-Coated Triathlon Tibial Baseplate—A Characterization of the Material Mechanical Properties", D00357-2, Version 5, 123 pages, 2012.
Randic et al; "Evaluation of the Stress Concentration Factor in Butt Welded Joints: A Comparative Study", Metals 2021, 11, 411, 10 pages.
Long et al, "Titanium alloys in total joint replacement—a materials science perspective", Biomaterials 19, Year 1998, pp. 1621-1639.
Amir et al; "Stress-constrained continuum topology optimization: a new approach based on elasto-plasticity"; Nov. 6, 2018, 30 pages.

* cited by examiner

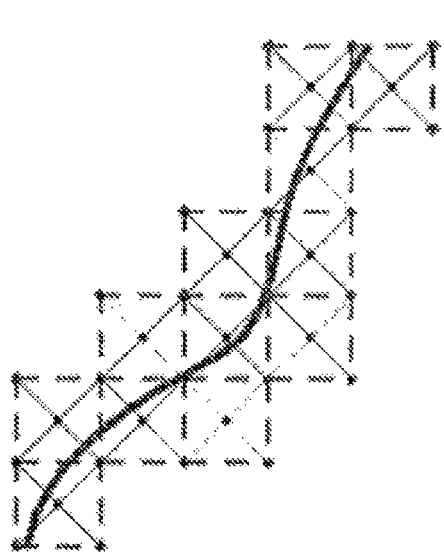
FIG. 2A
(Prior Art)
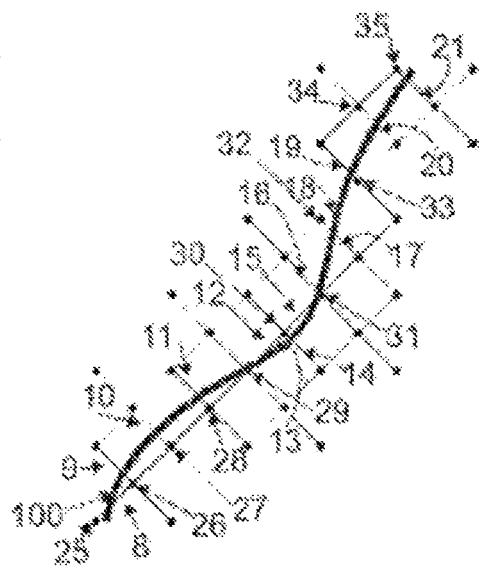
FIG. 2B
(Prior Art)
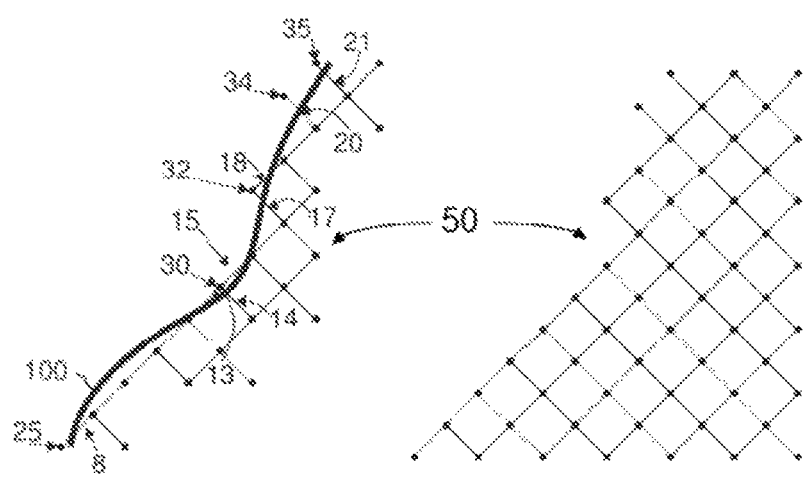
FIG. 3A
(Prior Art)
FIG. 3B
(Prior Art)

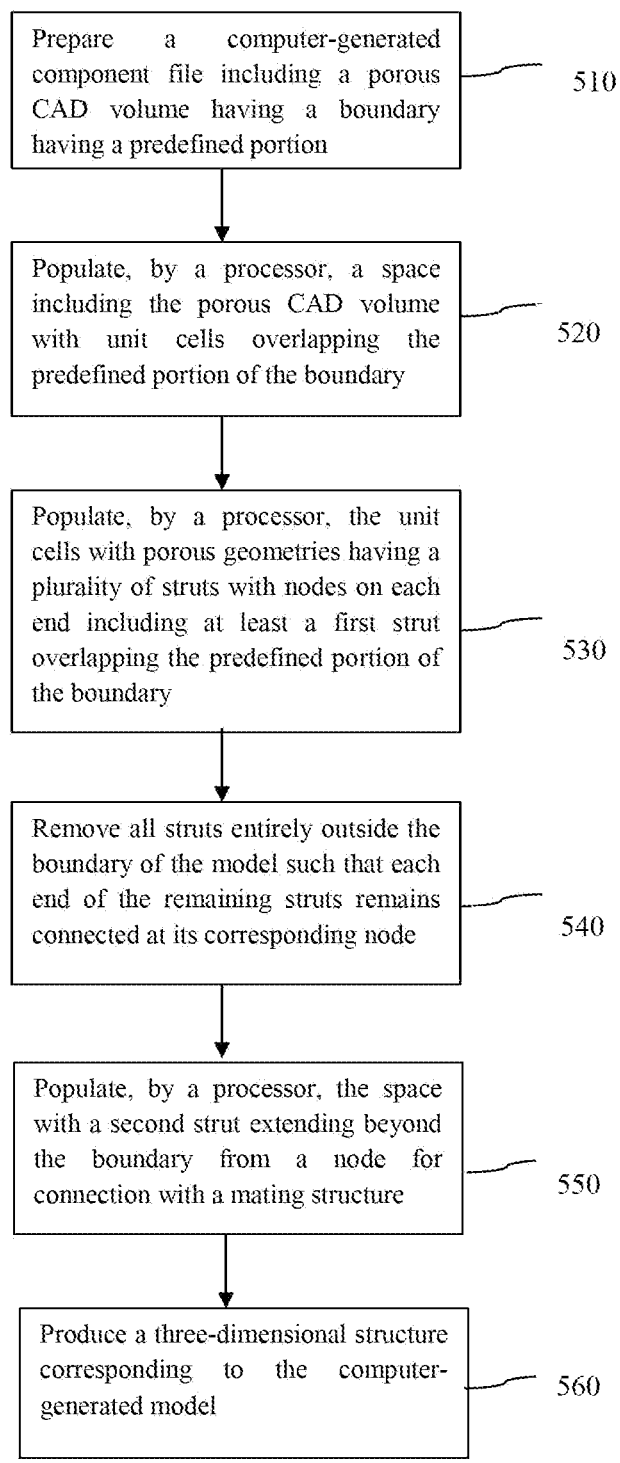

HIGH FATIGUE STRENGTH POROUS STRUCTURE

CROSS REFERENCE TO RELATED APPLICATIONS

The present application is a divisional of U.S. patent application Ser. No. 15/982,704, filed on May 17, 2018, now issued as U.S. Pat. No. 11,298,747, which claims the benefit of the filing date of U.S. Provisional Patent Application No. 62/508,058, filed on May 18, 2017, the disclosures of which are hereby incorporated herein by reference.

FIELD OF THE INVENTION

The present invention relates generally to three-dimensional porous structures and, in particular, to three-dimensional structures with porous surfaces having high fatigue strength and a process for the preparation of such structures.

BACKGROUND OF THE INVENTION

The field of additive layer manufacturing (ALM) has seen many important recent advances in the fabrication of articles directly from computer controlled databases. These advances have greatly reduced the time and expense required to fabricate articles, particularly in contrast to conventional machining processes in which a block of material, such as metal, is machined to engineering drawings.

Additive layer manufacturing has been used to produce various porous structures including, for example, medical implants. These structures are built in a layer-by-layer fashion in which individual layers often form portions of unit cells that have regular geometric shapes or irregular shapes having varied sides and dimensions. Various methods for producing a three-dimensional porous tissue ingrowth structure are disclosed in U.S. Pat. No. 9,180,010 filed Sep. 14, 2012 disclosing conformal manipulation of a porous surface; U.S. Pat. No. 9,456,901 filed Jul. 29, 2010 ("the '901 Patent") disclosing methods of creating porous surfaces having unit cells; and U.S. Pat. No. 7,537,664 filed Nov. 7, 2003 disclosing methods of beam overlap; the disclosures of each of which are incorporated herein by reference.

Advantageously, ALM allows for a solid substrate, e.g., a core of an implant, and an outer porous layer to be manufactured simultaneously, reducing manufacturing steps and materials, and thus costs, compared to conventional machining processes. However, current ALM techniques that form solid substrates and then porous layers onto the substrates create rough surfaces on the substrates that act as stress risers and result in an overall structure having relatively low fatigue strength. Due to their low fatigue strength, structures formed in this manner have an increased risk of fracture during use. Avoiding porous surfaces in high stress regions serves to increase the fatigue strength of such structures, but this approach leads to other undesirable properties of produced articles, e.g., by reducing available surfaces for bone in-growth in a medical implant which causes suboptimal implant fixation in the body.

Polishing the surfaces of devices is known to increase the fatigue strength of the devices. One well-known technique for polishing internal surfaces is abrasive flow machining, a process for polishing internal surfaces using a pressurized flow of a paste. The abrasive fluid flows through the interstices of the subject device and smooths its rough surfaces. Porous layers of solid-porous layer combinations formed by current ALM techniques have at least one of varying pore shapes and sizes, such as may be caused by the use of randomization techniques including those described in the '901 Patent, and relatively small pore sizes which may result in uneven or insufficient flow, respectively, of abrasive fluids during polishing. Such pore formations may lead to preferential polishing of a path through the largest pores which may not be along the interface of the solid and porous volumes, where the best surface finish is needed.

Thus, there is a need for a new process to form highly porous structures without sacrificing fatigue strengths.

BRIEF SUMMARY OF THE INVENTION

In accordance with an aspect, a computer-aided design (CAD) first model build structure may include unit cells that may be populated with porous geometries, each of the porous geometries may be made up of struts that extend to vertices of the unit cells and collectively define faces and intersect at nodes at the vertices. The porous geometries can be used to control the shape, type, degree, density, and size of porosity within the structure. The first model build structure may be subjected to conformal manipulation such that certain nodes lying outside a boundary are repositioned to lie on the boundary. The first model build structure may include connection elements, which may be a set of equally spaced-apart joining struts, extending from the nodes repositioned on the boundary. The connection elements may connect the first model build structure to a mating model build structure, which may be a solid CAD model build structure.

The porous geometries may include first faces that at least partially confront, i.e., face, the mating model build structure, in which the first faces may extend in a direction parallel to a central axis of the mating model build structure or the faces may extend in any non-parallel direction, and each first face is positioned directly in front of and projects onto the mating building structure. Each of the first faces may be connected to the mating model build structure by a single connection element extending from one of the nodes of the first faces on the boundary. In some arrangements, the first model build structure may be uniformly spaced from the boundary such that connection elements may have substantially equal lengths.

A tangible, fabricated porous structure having a solid base or core and corresponding to a combination of the first and mating model build structures may be formed layer by layer using ALM. Notably, this tangible structure would provide for an even flow of abrasive fluid along the porous-solid interface because of the joining struts of equal length. In this manner, a higher fatigue strength of the tangible structure may be achieved.

In accordance with another aspect, a porous apparatus may include a first layer and a second layer having a plurality of struts. A portion of the plurality of struts may define a porous geometry. The porous geometry may define a plurality of faces, at least one of the plurality of faces at least partially confronting the first layer. Each of the faces may be bounded by intersecting struts at vertices. Less than all of the vertices of each face at least partially confronting the first layer may be connected to the first layer by a strut, in which each such strut may be a first attachment strut.

In some arrangements, the first and second layers may be made of a metal. The metal preferably may be titanium, titanium alloys, stainless steel, cobalt chrome alloys, tantalum and niobium, or any combination thereof. In some arrangements, the porous geometry may be in the form of an octahedron, a dodecahedron, or a tetrahedron. In some arrangements, the first layer may be solid.

In some arrangements, additional struts of the plurality of struts may define additional porous geometries that each may define additional faces at least partially confronting the first layer. Each of the additional faces may be bounded by intersecting struts at vertices. Less than all of the vertices of each of the additional faces at least partially confronting the first layer may be connected by additional attachment struts to the first layer. The first attachment strut and the additional attachment struts may have the same length. In some such arrangements, the additional attachment struts may extend in the same direction. In some such arrangements, the additional attachment struts may extend along axes extending through a central axis of the first layer.

In accordance with another aspect, a porous apparatus includes a first layer and a second layer having a plurality of struts. Some of the struts define a first porous geometry. The first porous geometry is connected to the first layer by only a first attachment strut.

In some arrangements, the first and second layers may be made of a metal selected from the group consisting of titanium, titanium alloys, stainless steel, cobalt chrome alloys, tantalum and niobium. In some arrangements, the first porous geometry may be in the form of an octahedron, a dodecahedron, or a tetrahedron. In some arrangements, the first layer may be solid.

In some arrangements, additional struts of the plurality of struts may define additional porous geometries each connected to the first layer by only an additional attachment strut. The first attachment strut and the additional attachment struts may have the same length. In some such arrangements, the additional attachment struts may extend in the same direction. In some such arrangements, the additional attachment struts may each extend along an axis extending through a central axis of the first layer.

In some arrangements, the porous apparatus may be a medical implant.

In accordance with another aspect, a porous structure may be produced. In producing the porous structure, a first layer of a metal powder may be deposited onto a substrate. The first layer of the metal powder may be scanned with a high energy beam to form either one or both of a portion of a first section of the structure and a portion of a plurality of struts. The struts may define a porous geometry. The struts and the porous geometry may form a second section of the structure. Successive layers of the metal powder may be deposited onto respective previous layers of powder. Each of the successive layers of the powder may be scanned with the high energy beam until the first and second sections and the portion of the plurality of struts defining the porous geometry. The porous geometry may be attached to the first section by only a first attachment strut.

In some arrangements, the substrate may be separable from the porous structure. In some other arrangements, the substrate may be integral with the porous structure such that the substrate is inseparable from the porous structure. In some arrangements, the porous apparatus may be a medical implant.

In some arrangements, the high energy beam may be an electron beam. In some arrangements, the high energy beam may be a laser beam. In some arrangements, the first section of the structure may be solid. In some arrangements, additional struts may define additional porous geometries each attached to the first section by only an additional first attachment strut. The first attachment strut and the additional attachment struts may have the same length. In some such arrangements, the additional attachment struts may extend in the same direction. In some such arrangements, the additional attachment struts may each extend along an axis extending through a central axis of the structure.

In accordance with another aspect of the invention, a porous structure may be produced. In producing the porous structure, a first layer of a metal powder may be deposited onto a substrate. The first layer of the metal powder may be scanned with a high energy beam to form either one or both of a portion of a first section of the structure and a portion of a plurality of struts. The struts may define a porous geometry. The struts and the porous geometry may form a second section of the structure. Successive layers of the metal powder may be deposited onto respective previous layers of powder. Each of the successive layers of the powder may be scanned with the high energy beam until the portion of the first section and the portion of the plurality of struts defining the porous geometry are formed. The porous geometry may define a plurality of faces, at least one of the plurality of the faces at least partially confronting the first section of the structure. Each of the faces may be bounded by intersecting struts at vertices. Less than all of the faces of each face at least partially confronting the first section may be connected to the first section of the porous structure by a strut, in which each such strut may be a first attachment strut.

In some arrangements, the substrate may be separable from the porous structure. In some other arrangements, the substrate may be integral with the porous structure such that the substrate is inseparable from the porous structure. In some arrangements, the porous apparatus may be a medical implant.

In some arrangements, the first and second layers may be made of a metal. The metal preferably may be titanium, titanium alloys, stainless steel, cobalt chrome alloys, tantalum and niobium, or any combination thereof. In some arrangements, the high energy beam may be an electron beam. In some arrangements, the high energy beam may be a laser beam. In some arrangements, the first section of the structure may be solid.

In some arrangements, additional struts of the plurality of struts may define additional porous geometries that each may define additional faces at least partially confronting the first layer. Each of the additional faces may be bounded by intersecting struts at vertices. Less than all of the vertices of each of the additional faces at least partially confronting the first layer may be connected by additional attachment struts to the first layer. The first attachment strut and the additional attachment struts may have the same length. In some such arrangements, the additional attachment struts may extend in the same direction. In some such arrangements, the additional attachment struts may each extend along an axis extending through a central axis of the first layer.

In accordance with another aspect of the invention, a computer-generated model of a three-dimensional structure constructed of porous geometries may be prepared according to a process. In this process, a computer-generated component file including a porous CAD volume having a boundary may be prepared. A space may be populated by a processor. The space may include the porous CAD volume which may be populated by unit cells. The unit cells with porous geometries may be populated by a processor. A plurality of porous geometries may have a plurality of struts with nodes at each of the ends of the struts which may include a first strut overlapping the boundary. The first strut may have a length, a first node outside the porous CAD volume, and a second node inside the porous CAD volume.

All struts entirely outside the porous CAD volume may be removed such that each of the remaining struts is connected at its corresponding node. The space may be populated, by a processor, with a second strut extending beyond the boundary from a node for connection with a mating structure.

In some arrangements, the node from which the second strut extends beyond the boundary may define an intersection of two struts of a porous geometry on or confronting the boundary. In some arrangements, during the process, the first strut overlapping the boundary may be removed, by a processor, when the first node at the first end of the strut is further from the boundary than the second node at the second end of the first strut.

In some arrangements, the second node at the second end of the first strut may be connected to an adjacent strut inside the porous CAD volume. A closer of the first and the second nodes may be moved to a position along the boundary during the process. When the first node is the closer node, the length of the first strut may be changed such that the first strut remains connected to the first node. When the second node is the closer node, the length of the adjacent strut may be changed such that the first strut remains connected to the second node. When the second node is the closer node, the first node and the first strut overlapping the boundary may be removed.

In some arrangements, the second strut may be connected with the mating structure. In some arrangements, the mating structure may correspond to a solid or substantially solid structure. In some arrangements, a method of fabricating a porous structure may include three-dimensional (3-D) printing a three-dimensional structure having a shape and dimensions corresponding to the computer-generated model prepared.

In accordance with another aspect of the invention, a non-transitory computer-readable storage medium may have computer readable instructions of a program stored on the medium. The instructions, when executed by a processor, may cause the processor to perform a process of preparing computer-generated model of a three-dimensional structure constructed of porous geometries. In this process, a computer-generated component file including a porous CAD volume having a boundary may be prepared. A space including the porous CAD volume with unit cells may be populated by a processor. The unit cells may be populated, by a processor, with the porous geometries. A plurality of the porous geometries may have a plurality of struts that may have opposing ends. Each of the ends may be connected at a corresponding node. A first strut of the plurality of struts may overlap the boundary. The first strut may have a length, a first node at a first end outside the porous CAD volume, and a second node at a second end inside the porous CAD volume. All struts entirely outside the porous CAD volume may be removed, by a processor, such that each end of the remaining struts remains connected at its corresponding node. The space may be populated, by a processor, with a second strut extending beyond the boundary from a node for connection with a mating structure.

BRIEF DESCRIPTION OF THE DRAWINGS

A more complete appreciation of the subject matter of the present invention and the various advantages thereof may be realized by reference to the following detailed description, in which reference is made to the following accompanying drawings:

FIG. 2A illustrates a wireframe of porous geometries created within unit cells that intersect a boundary of a porous CAD volume, which models the porous portion of the structure to be manufactured up to the outer boundary of the porous portion, as known in the prior art;

FIG. 2B illustrates the nodes and the struts of the porous geometries within the unit cells of FIG. 2A;

FIGS. 3A and 3B illustrate the wireframe of the porous geometries of FIG. 2 after removing the full length of struts lying entirely outside the boundary of the porous CAD volume and removing the full length of struts overlapping the boundary that have outer nodes further from the boundary than their corresponding inner nodes as known in the prior art;

FIG. 8 is a process flow diagram in accordance with an embodiment.

DETAILED DESCRIPTION

Figure 1:
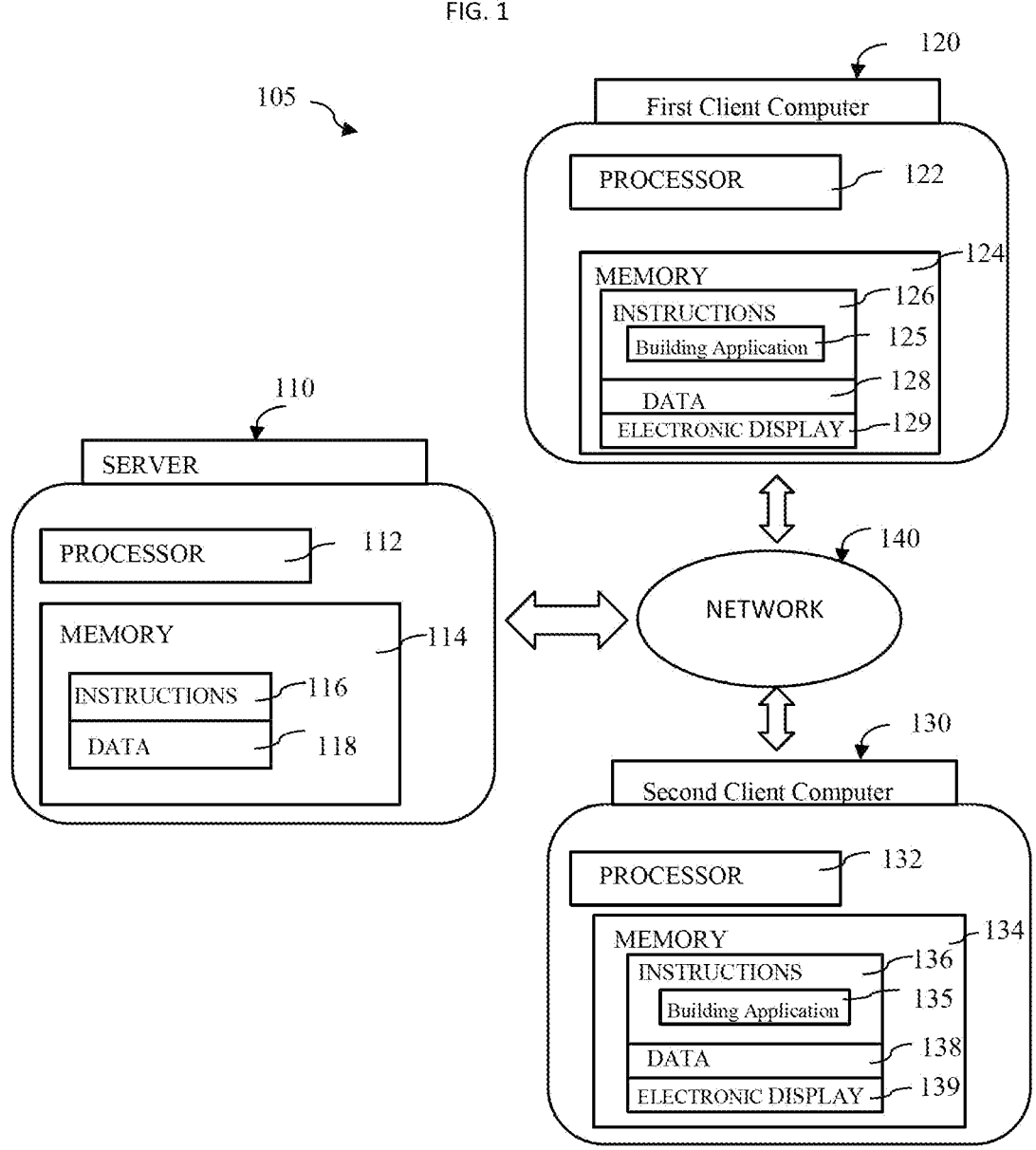
FIG. 1 is a functional diagram of a system in accordance with an exemplary embodiment.

FIG. 1 depicts system 105 that may be used to generate, store and share three-dimensional models of structures. System 105 may include at least one server computer 110, first client computer 120, and in some examples, second client computer 130. These computers may send and receive information via network 140. For example, a first user may generate a model on first client computer 120 which may be uploaded to server 110 and distributed via network 140 to second client computer 130 for viewing and modification by a second user.

Network 140, and intervening communication points, may comprise various configurations and protocols including the Internet, World Wide Web, intranets, virtual private networks, wide area networks, local networks, private networks using communication protocols proprietary to one or more companies, Ethernet, WiFi, and HTTP, and various combinations of the foregoing. Such communication may be facilitated by any device capable of transmitting data to and from other computers, such as modems (e.g., dial-up, cable or fiber optic) and wireless interfaces. Although only a few devices are depicted, a conventional system may include a large number of connected computers, with each computer being at a different communication point of the network.

Each of computers 110, 120, and 130 may include a processor and memory. For example, server 110 may include memory 114 which stores information accessible by processor 112, computer 120 may include memory 124 which stores information accessible by processor 122, and computer 130 may include memory 134 which stores information accessible by processor 132.

Processors 112, 122, 132 may be any conventional processor, such as commercially available CPUs. Alternatively, the processors may be dedicated controllers such as an ASIC, FPGA, or other hardware-based processor. Although shown in FIG. 1 as being within the same block, the processor and memory may comprise multiple processors and memories that may or may not be stored within the same physical housing. For example, memories may be a hard drive or other storage media located in a server farm of a network data center. Accordingly, references to a processor, memory, or computer will be understood to include references to a collection of processors, memories, or computers that may or may not operate in parallel.

The memories may include a first part storing applications or instructions 116, 126, 136 that may be executed by the respective processor. Instructions 116, 126, 136 may be any set of instructions to be executed directly (such as machine code) or indirectly (such as scripts) by the processor. In that regard, the terms "applications," "instructions," "steps" and "programs" may be used interchangeably herein.

The memories may also include a second part storing data 118, 128, 138 that may be retrieved, stored or modified in accordance with the respective instructions. The memory may include any type capable of storing information accessible by the processor, such as hard-drive, memory card, ROM, RAM, DVD, CD-ROM, write-capable, and read-only memories or various combinations of the foregoing, where applications 116 and data 118 are stored on the same or different types of media.

In addition to a processor, memory and instructions, client computers 120, 130 may have all of the components used in connection with a personal computer. For example, client computers 120, 130 may include respective electronic displays 129, 139 (e.g. a monitor having a screen, a touch screen, a projector, a television, a computer printer, or any other electrical device that is operable to display information), one or more user inputs (e.g. a mouse, keyboard, touch screen and/or microphone), speakers, and all of the components used for connecting these elements to one another.

Instructions 126, 136 of first and second client computers 120, 130 may include building applications 125, 135. For example, the building applications may be used by a user to create three-dimensional structures, described further herein. The building applications may be associated with a graphical user interface for displaying on a client computer in order to allow the user to utilize the functions of the building applications.

A building application may be a CAD three-dimensional modeling program or equivalent as known in the art. Available CAD programs capable of generating such a structure include Autodesk® AutoCAD®, Creo® by Parametric Technology Corporation (formerly Pro/Engineer), Siemens PLM Software NX™ (formerly Unigraphics), and CATIA® by Dassault Systèmes.

Data 118, 128, 138 need not be limited by any particular data structure. For example, such data may be stored in computer registers, in a relational database as a table having a plurality of different fields and records, or XML documents. The data may also be formatted into any computer-readable format, which preferably may be binary values, ASCII or Unicode. Further, the data may comprise any information sufficient to identify the relevant information, such as numbers, descriptive text, proprietary codes, pointers, references to data stored in other memories (including other network locations) or information that is used by a function to calculate the relevant data. For example, data 128 of first client computer 120 may include information used by building application 125 to create three-dimensional models.

In addition to the operations described above and illustrated in the figures, various other operations will now be described. It should be understood that the following operations do not have to be performed in the exact order described below. Instead, various steps may be handled in a different order or simultaneously. Steps may also be omitted or added unless otherwise stated herein.

An overall three-dimensional representation of a component may first be generated by preparing a CAD model. This overall CAD model may include one or more distinct CAD volumes, e.g., solid and porous CAD volumes, that are intended to be modeled by a model build structure which in turn used to manufacture a part as either solid or porous geometries or a combination of the two.

Solid CAD volumes may be sliced into layers of a predetermined thickness ready for hatching, re-merging with the porous volume (post-lattice generation) and subsequent manufacture.

Porous CAD volumes (the basic principles of which are detailed in FIGS. 2A and 2B) may be processed using bespoke software. In some examples, a model structure, such as model build structure 50 identified in FIGS. 3A and 3B is made up of a plurality of struts defining individual porous geometries which are organized within tessellated unit cells, e.g., porous geometries 55 identified in FIG. 2A which are organized within tessellated unit cells 60. Many designs of porous geometries are possible to impart various strength, surface, and/or other characteristics into the porous CAD volume. For example, these porous geometries can be used to control the shape, type, degree, density, and size of porosity within the structure. Such porous geometry designs may be bounded by unit cells that may be dodecahedral, octahedral, tetrahedral (diamond), as well as many other various shapes. Besides such regular geometric shapes, the cells of the present invention may be configured to have irregular shapes where various sides and dimensions have little if any repeating sequences. The cells, including the unit cells, may be configured to constructs that closely mimic the structure of trabecular bone, for instance. Porous geometries can be space filling, in which all the space within a three-dimensional object is filled with porous geometries but do not always fill the space of an object they are used to produce.

The first step in creating a porous CAD volume is to calculate a bounding box, a box with x, y, and z dimensions corresponding to, or slightly larger than, a predefined boundary of the porous CAD volume, which may be the entire boundary or a portion of a boundary. The bounding box is then divided into a number of cells, such as unit cells 60, defined by x, y, and z dimensions. Calculations are then performed during an interrogation on each individual cell 60 to ascertain if each cell is within or intersects the boundary of the porous CAD volume. If these conditions are satisfied for an individual cell, that cell is retained such as in the example of FIG. 2A, and if they are not satisfied, that cell is discarded. Once all cells have been interrogated, the overall porous geometry is populated within cells that have been retained, such as in the example of FIGS. 2A and 2B in which a collection of porous geometries 55, which together form model build structure 50, are populated within unit cells 60 that have been retained in a porous CAD volume.

Each of the individual porous geometries 55 is made up of struts, i.e., segments having a length. Nearly all of the struts meet at a node or intersection. The position of the nodes may be identified within an array of the data of the processor according to Cartesian, polar coordinates, or other user-defined coordinates.

In one example, a porous CAD volume is bounded by predefined boundary 100 that corresponds to the intended surface of a part to be formed. As shown in FIGS. 2A and 2B, some unit cells along predefined boundary 100 have overlapping struts that cross over the boundary. The struts have inner nodes within boundary 100 and outer nodes outside the boundary. To produce a porous structure having struts that terminate at boundary 100, each strut that intersects the boundary is either fully retained or removed depending on the distance of its nodes from boundary 100. Each strut having an outer node farther from boundary 100 than its inner node is fully removed. Whereas, each strut having an outer node closer to boundary 100 than its inner node is fully retained. In this example, with reference to FIGS. 2B, 3A, and 3B, struts 9-12, 16 and 19 are fully removed because their outer nodes are farther from the boundary than their inner nodes. Whereas, struts 8, 13-15, 17-18, and 20-21 are fully retained because outer nodes 25, 30, 32, 34, and 35, although outside the boundary 100, are still closer than their corresponding inner nodes.

Figure 4A:
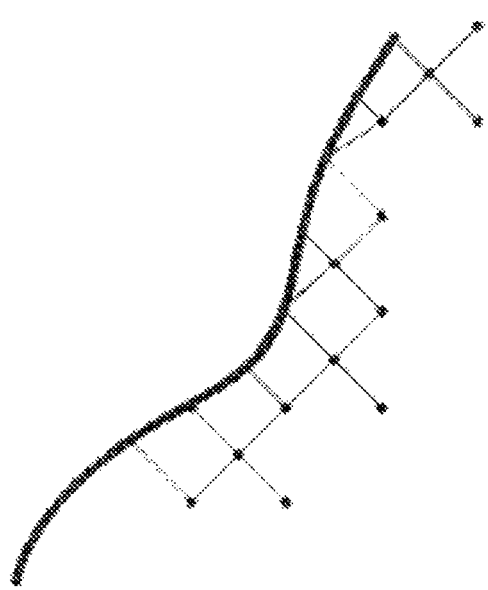
FIGS. 4A and 4B illustrate the wireframe of the porous geometries of FIG. 3 after repositioning of the nodes closest to the boundary to positions along the boundary of the porous CAD volume through conformal manipulation, as known in the prior art.
Figure 4B:
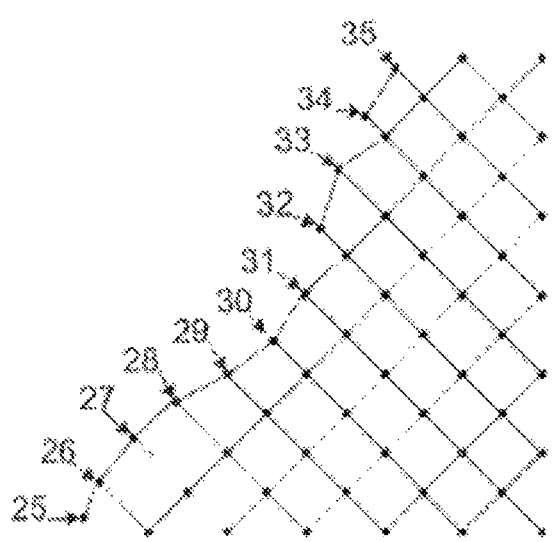

Still referring to this example, as shown in FIGS. 4A and 4B, after removal of the appropriate struts, the nodes closest to boundary 100, nodes 25-35, may be repositioned to lie on the boundary, and as such nodes 25-35 are conformal nodes. In some examples, the conformal nodes may be repositioned based on a mathematical calculation based on the original position of each of these nodes, the distance from the boundary of each of these nodes, or based on the original length of the struts attached to these nodes that overlap the boundary, or based on both of these values. In this way, the shape of the structure may be maintained or at least substantially maintained when having conformal nodes along the boundary.

Upon repositioning of nodes 25-35, the struts connected to these nodes may be lengthened or shortened to maintain connectivity with the repositioned nodes. Alternatively, nodes 25-35 may not be repositioned but rather discarded and replaced by new nodes. Likewise, the struts originally connected to nodes 25-35 may be discarded and replaced by new struts that are longer or shorter than the original struts to provide connectivity with the corresponding repositioned nodes. In this manner, the unit cells and nodes experience conformal manipulation.

In another example, only struts having both nodes inside the boundary may be retained. The node closest to the boundary may then be repositioned to lie on the boundary and any adjacent strut previously connected to the repositioned node may be lengthened or shortened to maintain connection with the repositioned node, as described above. Alternatively, the nodes and struts may be replaced with new nodes and struts, as above.

The use of polar or spherical coordinates may be preferred to the use of Cartesian coordinates when a surface of a model build structure to be formed is curvate or cylindrical. In this manner, nodes repositioned on a boundary may be positioned at the same angle defining a replaced node but at a different radius from the origin of a polar coordinate system being used to create a model build structure. However, other user-defined node positioning system also may be used to form a model build structure having nodes along an outer boundary that fit the contours of the outer boundary of the component being modeled.

Figure 5A:
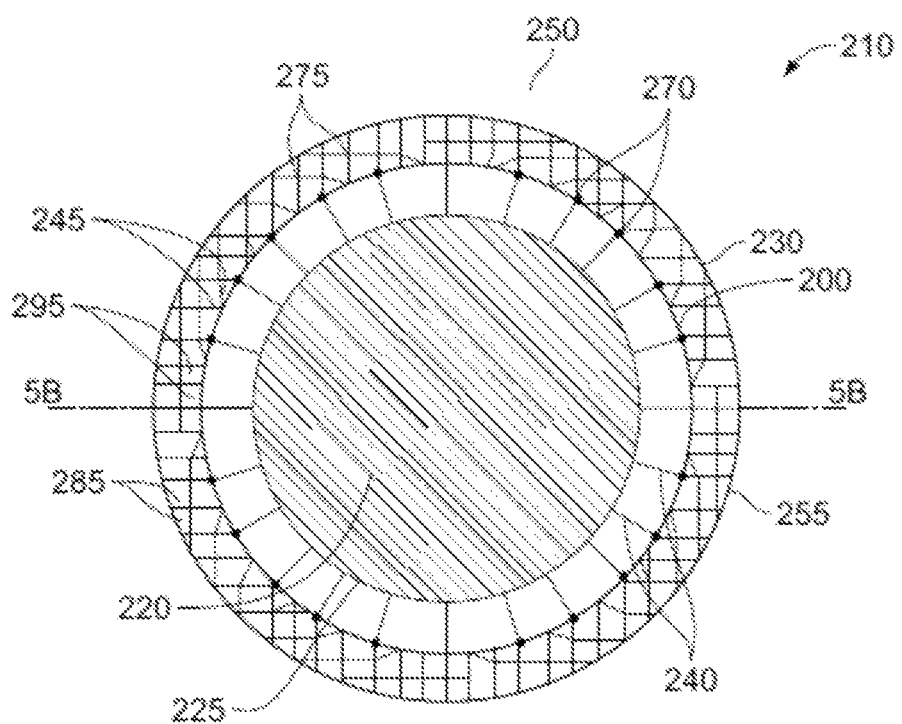
FIGS. 5A and 5B are plan and side cross-sectional views of a solid CAD volume surrounded by a porous CAD volume of a cylindrical geometry, in accordance with an embodiment.
Figure 5B:
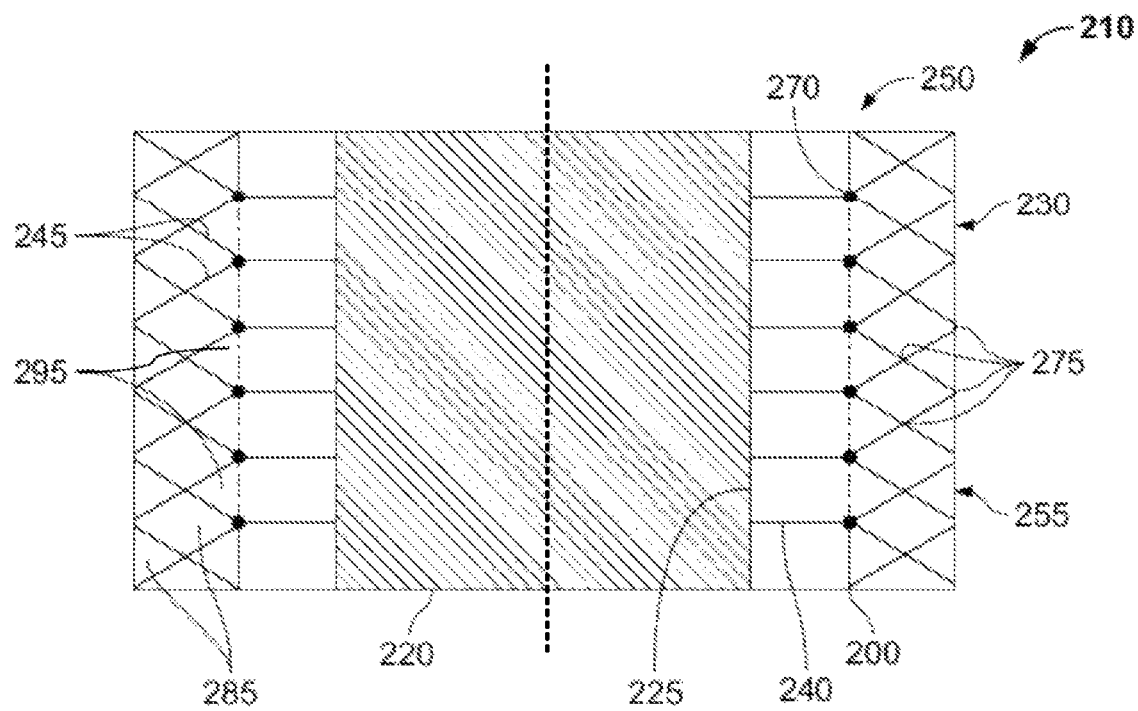

Referring now to FIGS. 5A and 5B, porous structure 210, which in some arrangements may be in the form of a medical implant, includes first layer or section 220 and porous model build structure 250 that connects to the first layer at interface 225. First layer 220 forms a base or core of structure 210 and, as in this example, may be solid, although in alternative arrangements the first layer may be at least partially porous. Porous model build structure 250 includes porous layer 230 and joining struts 240 that connect the model build structure to first layer 220 at interface 225. Porous layer 230 includes a plurality of porous geometries 255.

Porous geometries 255 may be modeled using available CAD programs, which preferably may be any of those described previously herein, through the use of cells in the manner described previously herein. In the example shown, octahedral unit cells may be used to form porous geometries 255. In alternative arrangements, other cell designs may be utilized, which may, in some arrangements, be either or both octahedral and dodecahedral unit cells. In the example shown, each porous geometry 255 includes a plurality of struts 245 that intersect at vertices defining boundary nodes 270 along circular boundary 200 and at vertices defining nodes 275 at positions away from the boundary to define faces 285 of the unit cells facing away from first layer 220 and faces 295 at least partially confronting first layer 220.

Porous geometries 255 along boundary 200 define faces 295 that at least partially confront first layer 220 and have struts 245 connected at one of their ends to boundary nodes 270, which in this example have been repositioned onto porous boundary 200 in the same manner as nodes 25-35 were repositioned along boundary 100 as described above with respect to model build structure 50. Each face 295 at least partially confronting first layer 220 is connected to the first layer by single joining strut 240 extending from one of the boundary nodes 270. In this manner, as boundary 200 is equidistant about its circumference from first layer 220, boundary nodes 270 are set at substantially equal distances from first layer 220, and as a result, joining struts 240 connecting porous layer 230 to first layer 220 are all of substantially equal lengths.

With this configuration, abrasive polishing material can flow evenly along an interface of a fabricated structure corresponding to interface 225 of structure 210 at a junction of a core and a porous section of the fabricated structure corresponding to first layer 220 and porous model build structure 250, respectively. In this manner, a higher fatigue strength of the fabricated structure corresponding to structure 210 may be achieved.

Unlike nodes 270, nodes 275 are not connected to any joining strut 240 extending to first layer 220. In this manner, less than all of the nodes of each porous geometry 255 are connected to first layer 220.

Although the joining struts may be of substantially equal lengths, such as in the example of FIGS. 5A and 5B, the joining struts may extend in any possible build direction. In the example of FIGS. 5A and 5B, joining struts 240 extend in parallel planes perpendicular to a central axis of first layer 220 and of structure 210 (shown in dashed lines in FIG. 5B) and in various directions ranging between approximately 0 degrees and 360 directions about a circumference of boundary layer 200 and first layer 220. Alternatively, joining struts 240 may be defined as being oriented in directions defined by the intersection of a plane defined by a vector normal to their respective attachment points on the first layer 220 and orthogonal to boundary layer 200, which may correspond to a build surface. As further shown in FIG. 5A, in some such arrangements, joining struts 240 all extend along axes extending through a central axis of first layer 220.

Figure 6:
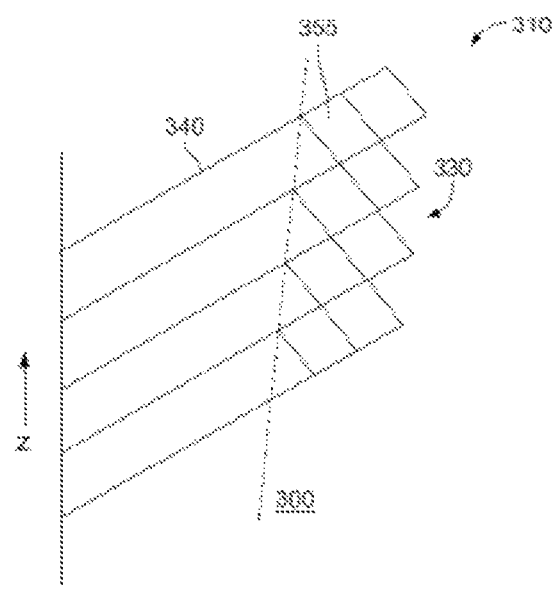
FIG. 6 is a partial cross-sectional side view of a porous CAD volume along an edge of a solid CAD volume aligned along a Z-axis, in accordance with another embodiment.
Figure 7:
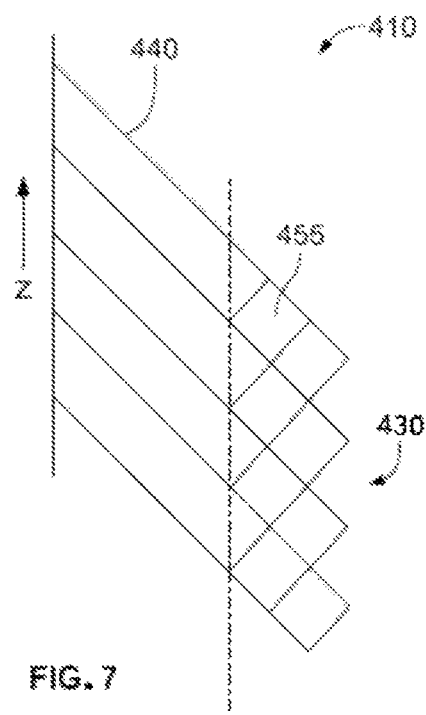
FIG. 7 is a partial cross-sectional side view of a porous CAD volume along an edge of a solid CAD volume aligned along a Z-axis in accordance with another embodiment.

Referring to FIGS. 6 and 7, in other examples, the joining struts may extend in the same direction. As shown in FIG. 6, structure 310 includes joining struts 340 extending in an upward direction along the z-axis and connecting first layer 320 to porous layer 330. In contrast, as shown in FIG. 7, structure 410 includes joining struts 440 extending in a downward direction along the z-axis and connecting first layer 420 to porous layer 430. Alternatively, joining struts 340, 440 may be defined as being oriented in directions defined by the intersection of a plane oriented 45 degrees upward or downward from its attachment point on first layers 320, 420 towards the boundary nodes along boundaries 300, 400, respectively. In another example, adjacent joining struts may extend in an alternating upward-downward pattern. In this manner, interconnecting pore size may be larger at the interface of the porous surface and the first layer, which may be a core. The larger interconnecting pore size may preferably allow a greater amount of abrasive material to flow along the interface.

In some arrangements, the joining struts, such as joining struts 240, 340, 440 may be larger or smaller in diameter than other struts of a model build structure, such as model build structure 250. In some arrangements, the joining struts, such as joining struts 240, 340, 440 may be longer or shorter than other struts of a model build structure, such model build structure 250. In some arrangements, more than a single joining strut, such as joining struts 240, 340, 440, may extend from vertices of intersecting struts defining faces of a porous geometry at least partially confronting the first layer, e.g., core, of a structure, but in such arrangements, less than all of the vertices of each face of the porous geometry at least partially confronting the first layer may be connected by a strut to the first layer.

Each of structures 210, 310, and 410 may be formed in a layer-by-layer fashion during an ALM, i.e., 3D printing, process using a high energy beam, which may be a selective laser sintering (SLS) or selective laser melting (SLM) process as described in U.S. Pat. Nos. 7,537,664; 8,728,387; and 9,456,901, the disclosures of each of which are hereby incorporated by reference herein. A first layer or portion of a layer of metal powder is deposited onto a substrate, which, in some arrangements, may be a core of a structure, a base, or a work platform, and then scanned with the high energy beam so as to sinter or melt the powder and create a portion of a plurality of predetermined porous geometries, such as porous geometries 255, 355, 455. Successive layers of the metal powder are then deposited onto previous layers of the metal powder and also respectively scanned with the high energy beam prior to the deposition of subsequent layers of the metal powder. The scanning and depositing of successive layers of the metal powder continues the building process of the predetermined porous geometries. Such continuation of the building process refers not only to a continuation of a predetermined porous geometry from a previous layer but also a beginning of a new predetermined porous geometry as well as or instead of the completion of a predetermined porous geometry, depending on the desired characteristics of the structure to be fabricated.

The structures formed using this process may be partially porous and, if desired, have interconnecting pores to provide an interconnecting porosity. The base or core may be fused to the 3D-printed structure, which may be a porous layer or section of the fabricated structure. At least one of the base or core and the 3D-printed structure preferably may be made of any of cobalt chrome alloy, titanium or alloy, stainless steel, niobium and tantalum. Thus, a mixture of desired mixed materials may be employed.

The high energy beam preferably may be an electron beam (e-beam) or laser beam and may be applied continuously to the powder or pulsed at a predetermined frequency. In some arrangements, the use of a laser or e-beam melting process may preclude the requirement for subsequent heat treatment of the structure fabricated by the additive manufacturing process, thereby preserving the initial mechanical properties of the core or base metal when fused to the fabricated structure. The high energy beam is emitted from a beam-generating apparatus to heat the metal powder sufficiently to sinter and preferably to at least partially melt or melt the metal powder. High energy beam generation equipment for manufacturing such structures may be one of many currently available including the MCP REALIZER, the EOS M270, TRUMPF TRUMAFORM 250, the ARCAM EBM S12, and the like. The beam generation equipment may also be a custom-produced laboratory device.

The pore density, pore size and pore size distribution may be controlled from one location on the structure to another. It is important to note that successive powder layers may differ in porosity by varying factors used for laser scanning powder layers. Additionally, the porosity of successive layers of powder may be varied by either creating a specific type of unit cell or manipulating various dimensions of a given unit cell. In some arrangements, the porosity may be a gradient porosity throughout at least a portion of the fabricated structure. The beam generation equipment may be programmed to proceed in a random generated manner to produce an irregular porous construct but with a defined level of porosity. Pseudo-random geometries may be formed by applying a perturbation to the vertices of porous geometries when preparing model build structures corresponding to the 3D structure to be fabricated. In this manner, the porous geometries may be randomized.

In fabricating a structure corresponding to porous structure 200, a first layer of metal powder may be deposited and scanned by a high energy beam to form a first section of the structure corresponding to first layer 220 of structure 200. The first section of the structure may form a base or core of the structure, which as shown may be solid, but in alternative arrangements may be at least partially porous.

Successive layers of the metal powder are then deposited onto the previous layers of the metal powder and then respectively scanned with the high energy beam prior to deposition of subsequent layers of the metal powder to form a plurality of struts defining porous geometries corresponding to the plurality of struts 245 defining porous geometries 255 of model build structure 250. In this manner, the fabricated structure is formed as a three-dimensional structure corresponding to porous structure 200 in which the struts corresponding to the plurality of struts 245 intersect at vertices corresponding to nodes 270, 275, which define faces of the porous geometries corresponding to porous geometries 255. As a result, the porous geometries of the fabricated structure corresponding to the porous geometries 255 have faces that at least partially confront the first section corresponding to first layer 220 of structure 200. Each of the fabricated faces is connected to the first section by a single joining strut corresponding to single joining strut 240 extending to the first section from a vertex of a face partially confronting the first section and corresponding to one of the nodes 270.

Due to the correspondence of the joining struts of the fabricated structure to joining struts 240 of structure 200, the joining struts of the fabricated structure all have substantially equal lengths. This equivalency eliminates a preferential path for abrasive fluid to flow between the porous section of the fabricated structure corresponding to model build structure 250 of porous structure 200 and the first section of the fabricated structure during polishing the first section. In this manner, the fatigue strength of the fabricated structure may be increased.

Although the joining struts are preferably of substantially equal lengths to enhance polishing of the first section of the fabricated structure, the joining struts of the fabricated structure may correspond to any of joining struts 240, 340, 440 and thus may extend in different build directions.

Referring now to FIG. 8, a computer-generated component file is prepared at block 510. The component file includes a porous CAD volume with a boundary having at least one predefined portion. At block 520, a space that includes the porous CAD volume is populated, by a processor, with unit cells that overlap the predefined portion of the boundary. Such a space may be defined by sets of coordinates, such as Cartesian, polar, or spherical coordinates. At block 530, the unit cells are populated, by a processor, with porous geometries. Within the porous geometries may be a plurality of struts. At least one end of the struts may be attached to a node. As further shown at block 530, at least one of the struts overlaps the predefined portion of the boundary. Such a strut has a length, one node outside the porous CAD volume, and one node inside the porous CAD volume. At block 540, any struts entirely outside the predefined portion of the boundary are removed. In some arrangements, any struts outside the entire boundary are removed. At block 550, the space is populated, by a processor, with a second strut extending beyond the boundary from a node for connection with a mating structure. In this manner, a computer-generated model of a three-dimensional structure constructed of porous geometries is prepared. At optional block 560, a tangible three-dimensional structure having a shape corresponding to the computer-generated model may be produced. The shape of the three-dimensional structure may be in the form of an at least partially geometric lattice structure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention. In this regard, the present invention encompasses numerous additional features in addition to those specific features set forth in the claims below.

The invention claimed is:

1. A porous apparatus comprising:
a first layer; and
a second layer having a plurality of struts, at least some of the struts defining a porous geometry, the porous geometry defining a plurality of faces, at least one of the plurality of the faces at least partially confronting the first layer, each of the faces bounded by intersecting struts at vertices,
wherein less than all of the vertices of each face of the porous geometry at least partially confronting the first layer are connected by a strut to the first layer, each such strut being a first attachment strut.

2. The apparatus of claim 1, wherein the first and second layers are made of a metal selected from the group consisting of titanium, titanium alloys, stainless steel, cobalt chrome alloys, tantalum and niobium.

3. The apparatus of claim 1, wherein the porous geometry is in the form of an octahedron, a dodecahedron, or a tetrahedron.

4. The apparatus of claim 1, wherein the first layer is solid.

5. The apparatus of claim 1, wherein additional struts of the plurality of struts define additional porous geometries that each define a plurality of additional faces at least partially confronting the first layer, each of the additional faces bounded by intersecting struts at vertices, wherein less than all of the vertices of each of the additional faces of the additional porous geometries at least partially confronting the first layer are connected by additional attachment struts to the first layer, and wherein the first attachment strut and the additional attachment struts are the same length.

6. The apparatus of claim 5, wherein the additional attachment struts extend in the same direction.

7. The apparatus of claim 5, wherein the additional attachment struts extend along axes extending through a central axis of the first layer.

8. A porous apparatus comprising:
a first layer; and
a second layer having a plurality of struts, some of the struts defining a first porous geometry,
wherein the first porous geometry is connected to the first layer by only a first attachment strut.

9. The apparatus of claim 8, wherein the first and second layers are made of a metal selected from the group consisting of titanium, titanium alloys, stainless steel, cobalt chrome alloys, tantalum and niobium.

10. The apparatus of claim 8, wherein the first porous geometry is in the form of an octahedron, a dodecahedron, or a tetrahedron.

11. The apparatus of claim 8, wherein the first layer is solid.

12. The apparatus of claim 8, wherein additional struts of the plurality of struts define additional porous geometries each connected to the first layer by only an additional attachment strut, and wherein the first attachment strut and the additional attachment struts have the same length.

13. The apparatus of claim 12, wherein the additional attachment struts extend in the same direction.

14. The apparatus of claim 12, wherein the additional attachment struts extend along axes extending through a central axis of the first layer.

* * * * *